United States Patent
Myrick et al.

(10) Patent No.: US 8,345,234 B2
(45) Date of Patent: Jan. 1, 2013

(54) SELF CALIBRATION METHODS FOR OPTICAL ANALYSIS SYSTEM

(75) Inventors: Michael L. Myrick, Irmo, SC (US); Robert P. Freese, Pittsboro, NC (US); David L. Perkins, Irmo, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 351 days.

(21) Appl. No.: 12/094,205

(22) PCT Filed: Mar. 10, 2006

(86) PCT No.: PCT/US2006/008952
§ 371 (c)(1),
(2), (4) Date: Dec. 15, 2008

(87) PCT Pub. No.: WO2007/061436
PCT Pub. Date: May 31, 2007

(65) Prior Publication Data
US 2009/0316150 A1    Dec. 24, 2009

Related U.S. Application Data

(60) Provisional application No. 60/740,045, filed on Nov. 28, 2005.

(51) Int. Cl.
*G01J 3/00* (2006.01)
(52) U.S. Cl. .................................... 356/300
(58) Field of Classification Search .......... 356/319, 356/411, 435
See application file for complete search history.

(56) References Cited

U.S. PATENT DOCUMENTS

| | | | |
|---|---|---|---|
| 3,632,435 A | 1/1972 | Eriksson et al. |
| 3,717,078 A | 2/1973 | Ogura |
| 3,761,724 A | 9/1973 | Dennis |
| 4,084,880 A | 4/1978 | Clow |
| 4,118,106 A | 10/1978 | Leith |
| 4,499,378 A | 2/1985 | Miyatake et al. |
| 4,595,832 A | 6/1986 | LaDelfe et al. |
| 4,607,914 A | 8/1986 | Fienup |

(Continued)

FOREIGN PATENT DOCUMENTS
EP    1969326 A1    9/2008
(Continued)

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.

(Continued)

*Primary Examiner* — Kara E Geisel
(74) *Attorney, Agent, or Firm* — Haynes and Boone, LLP (57) ABSTRACT

Disclosed is a system and methodologies for providing self-calibration in an optical analysis system. Illumination light is directed toward a material to be sampled while provisions are made to modify the characteristics of at least a portion of the illumination light falling on a reference detector. The modified characteristics may include light presence and/or spectral characteristics. Light presence may be modified by rotating or moving mirror assemblies to cause light to fall on either a sample detector or a reference detector while spectral characteristics may be modified by placing materials having known spectral characteristics in the path of the illumination light.

37 Claims, 4 Drawing Sheets

U.S. PATENT DOCUMENTS

| | | | |
|---|---|---|---|
| 4,687,335 A | 8/1987 | Zupanick et al. | |
| 4,687,337 A | 8/1987 | Stewart et al. | |
| 4,704,536 A | 11/1987 | Sugiyama et al. | |
| 4,821,338 A | 4/1989 | Naruse et al. | |
| 4,891,574 A | 1/1990 | Nagaya et al. | |
| 4,917,958 A | 4/1990 | Akai et al. | |
| 4,931,660 A * | 6/1990 | Mayer | 356/440 |
| 4,934,782 A | 6/1990 | Soffer et al. | |
| 4,968,148 A | 11/1990 | Chow et al. | |
| 4,981,332 A | 1/1991 | Smith | |
| 5,005,946 A | 4/1991 | Brandstetter | |
| 5,029,245 A | 7/1991 | Keranen et al. | |
| 5,071,526 A | 12/1991 | Pletcher et al. | |
| 5,090,807 A | 2/1992 | Tai | |
| 5,103,340 A | 4/1992 | Dono et al. | |
| 5,137,364 A | 8/1992 | McCarthy | |
| 5,150,236 A | 9/1992 | Patel | |
| 5,194,921 A | 3/1993 | Tambo et al. | |
| 5,223,715 A | 6/1993 | Taylor | |
| 5,259,381 A | 11/1993 | Cheung et al. | |
| 5,289,289 A | 2/1994 | Nagaski | |
| 5,321,539 A | 6/1994 | Hirbayashi et al. | |
| 5,332,901 A * | 7/1994 | Eckles et al. | 356/437 |
| 5,406,082 A | 4/1995 | Pearson et al. | |
| 5,412,465 A | 5/1995 | Baylor et al. | |
| 5,424,545 A | 6/1995 | Block et al. | |
| 5,459,677 A | 10/1995 | Kowalski et al. | |
| 5,479,164 A | 12/1995 | Yorks et al. | |
| 5,504,332 A | 4/1996 | Richmond et al. | |
| 5,513,022 A | 4/1996 | Son et al. | |
| 5,555,128 A | 9/1996 | Khoury et al. | |
| 5,622,868 A | 4/1997 | Clarke et al. | |
| 5,641,962 A | 6/1997 | Perry et al. | |
| 5,710,655 A | 1/1998 | Rumbaugh et al. | |
| 5,717,605 A | 2/1998 | Komiya et al. | |
| 5,734,098 A | 3/1998 | Kraus et al. | |
| 5,737,076 A | 4/1998 | Glaus et al. | |
| 5,747,806 A | 5/1998 | Khalil et al. | |
| 5,750,994 A | 5/1998 | Schlager | |
| 5,760,399 A | 6/1998 | Trygstad | |
| 5,771,096 A | 6/1998 | Andersen | |
| 5,781,289 A | 7/1998 | Sabsabi et al. | |
| 5,799,231 A | 8/1998 | Gates et al. | |
| 5,828,492 A | 10/1998 | Moser et al. | |
| 5,831,742 A | 11/1998 | Watson et al. | |
| 5,905,571 A | 5/1999 | Butler et al. | |
| 5,939,717 A | 8/1999 | Mullins | |
| 5,941,821 A | 8/1999 | Chou | |
| 5,945,676 A | 8/1999 | Khalil et al. | |
| 5,946,088 A | 8/1999 | Aldridge | |
| 5,946,089 A | 8/1999 | Duer | |
| 5,991,048 A | 11/1999 | Karlson et al. | |
| 6,006,585 A | 12/1999 | Forster | |
| 6,040,914 A | 3/2000 | Bortz et al. | |
| 6,124,937 A | 9/2000 | Mittenzwey et al. | |
| 6,137,108 A | 10/2000 | DeThomas et al. | |
| 6,176,323 B1 | 1/2001 | Weirich et al. | |
| 6,198,531 B1 | 3/2001 | Myrick et al. | |
| 6,304,854 B1 | 10/2001 | Harris | |
| 6,317,648 B1 | 11/2001 | Sleep et al. | |
| 6,347,131 B1 | 2/2002 | Gusterson | |
| 6,350,389 B1 | 2/2002 | Fujishima et al. | |
| 6,420,708 B2 | 7/2002 | Wilks, Jr. et al. | |
| 6,430,513 B1 | 8/2002 | Wang et al. | |
| 6,437,326 B1 | 8/2002 | Yamate et al. | |
| 6,469,785 B1 | 10/2002 | Duveneck et al. | |
| 6,476,384 B1 | 11/2002 | Mullins et al. | |
| 6,490,035 B1 | 12/2002 | Folestad et al. | |
| 6,517,230 B1 | 2/2003 | Afnan et al. | |
| 6,522,945 B2 | 2/2003 | Sleep et al. | |
| 6,529,276 B1 | 3/2003 | Myrick | |
| 6,573,999 B1 | 6/2003 | Yang | |
| 6,600,560 B2 | 7/2003 | Mikkelsen et al. | |
| 6,621,574 B1 * | 9/2003 | Forney et al. | 356/301 |
| 6,630,663 B2 | 10/2003 | Murphy et al. | |
| 6,667,802 B2 | 12/2003 | Faus et al. | |
| 6,690,464 B1 | 2/2004 | Lewis et al. | |
| 6,697,195 B2 | 2/2004 | Weber et al. | |
| 6,707,043 B2 | 3/2004 | Coates et al. | |
| 6,711,503 B2 | 3/2004 | Haaland | |
| 6,737,654 B2 | 5/2004 | Ducourant | |
| 6,741,335 B2 | 5/2004 | Kinrot et al. | |
| 6,748,334 B1 | 6/2004 | Perez et al. | |
| 6,765,212 B2 | 7/2004 | Goetz et al. | |
| 6,771,369 B2 | 8/2004 | Rzasa et al. | |
| 6,776,517 B2 | 8/2004 | Afnan et al. | |
| 6,798,518 B2 | 9/2004 | Difoggio et al. | |
| 6,853,447 B2 | 2/2005 | Goetz | |
| 6,870,629 B1 | 3/2005 | Vogel et al. | |
| 6,952,267 B2 | 10/2005 | Rarac | |
| 6,980,285 B1 | 12/2005 | Hansen | |
| 6,982,431 B2 | 1/2006 | Modlin et al. | |
| 6,995,840 B2 | 2/2006 | Hagler | |
| 7,006,214 B2 | 2/2006 | Rzasa et al. | |
| 7,123,844 B2 | 10/2006 | Myrick | |
| 7,138,156 B1 | 11/2006 | Myrick et al. | |
| 7,145,145 B2 | 12/2006 | Benson | |
| 7,173,239 B2 | 2/2007 | DiFoggio | |
| 7,245,374 B2 | 7/2007 | Hendriks | |
| 7,271,883 B2 | 9/2007 | Newell et al. | |
| 7,348,493 B2 | 3/2008 | Osanai et al. | |
| 7,399,968 B2 | 7/2008 | Lewis et al. | |
| 7,405,825 B2 | 7/2008 | Schuurmans et al. | |
| 7,411,729 B2 | 8/2008 | Lyama et al. | |
| 7,569,354 B2 | 8/2009 | Okano et al. | |
| 7,623,233 B2 | 11/2009 | Freese et al. | |
| 7,652,767 B2 | 1/2010 | Harsh et al. | |
| 7,671,973 B2 | 3/2010 | Van Beek et al. | |
| 7,697,141 B2 | 4/2010 | Jones et al. | |
| 7,853,104 B2 | 12/2010 | Oota et al. | |
| 7,889,346 B2 | 2/2011 | Myrick et al. | |
| 7,911,605 B2 | 3/2011 | Myrick et al. | |
| 7,920,258 B2 | 4/2011 | Myrick et al. | |
| 7,993,276 B2 | 8/2011 | Nazarian et al. | |
| 2001/0034064 A1 | 10/2001 | Turner et al. | |
| 2001/0055116 A1 * | 12/2001 | Maczura et al. | 356/326 |
| 2002/0008215 A1 | 1/2002 | Evans | |
| 2002/0050567 A1 | 5/2002 | Boudet et al. | |
| 2002/0071118 A1 | 6/2002 | Shinbori et al. | |
| 2002/0108892 A1 | 8/2002 | Goetz et al. | |
| 2002/0109094 A1 | 8/2002 | Goetz et al. | |
| 2002/0154315 A1 | 10/2002 | Myrick | |
| 2003/0056581 A1 | 3/2003 | Turner et al. | |
| 2003/0059820 A1 | 3/2003 | Vo-Dinh | |
| 2003/0071988 A1 | 4/2003 | Smith et al. | |
| 2003/0094495 A1 | 5/2003 | Knowles et al. | |
| 2003/0111606 A1 | 6/2003 | Berghmans et al. | |
| 2003/0117628 A1 | 6/2003 | Harju et al. | |
| 2003/0202179 A1 | 10/2003 | Larsen et al. | |
| 2004/0012782 A1 | 1/2004 | Mason et al. | |
| 2004/0106098 A1 | 6/2004 | Chen et al. | |
| 2004/0160601 A1 | 8/2004 | Womble et al. | |
| 2004/0197850 A1 | 10/2004 | Baer et al. | |
| 2004/0227086 A1 | 11/2004 | Haug et al. | |
| 2005/0032235 A1 | 2/2005 | Tummala et al. | |
| 2005/0077476 A1 | 4/2005 | Poteet et al. | |
| 2005/0087132 A1 | 4/2005 | Dickey et al. | |
| 2005/0167264 A1 | 8/2005 | Sternbergh et al. | |
| 2005/0251289 A1 | 11/2005 | Bonney et al. | |
| 2005/0264815 A1 * | 12/2005 | Wechsler et al. | 356/440 |
| 2005/0288906 A1 | 12/2005 | Drennen, III et al. | |
| 2006/0035018 A1 | 2/2006 | Sakurai et al. | |
| 2006/0051036 A1 | 3/2006 | Treado et al. | |
| 2006/0055919 A1 * | 3/2006 | Lee et al. | 356/301 |
| 2006/0093523 A1 | 5/2006 | Norman | |
| 2006/0142955 A1 | 6/2006 | Jones et al. | |
| 2006/0153492 A1 | 7/2006 | Treves et al. | |
| 2006/0158734 A1 | 7/2006 | Schuurmans et al. | |
| 2006/0169902 A1 | 8/2006 | Watanabe | |
| 2006/0197015 A1 | 9/2006 | Sterling et al. | |
| 2006/0276697 A1 | 12/2006 | Demuth et al. | |
| 2007/0035737 A1 | 2/2007 | Andrews et al. | |
| 2007/0137292 A1 | 6/2007 | Xian et al. | |
| 2007/0201136 A1 | 8/2007 | Myrick | |
| 2007/0282647 A1 | 12/2007 | Freese et al. | |
| 2007/0294094 A1 | 12/2007 | Alessandrini et al. | |
| 2008/0111064 A1 | 5/2008 | Andrews et al. | |

| | | | |
|---|---|---|---|
| 2008/0231849 A1 | 9/2008 | Myrick | |
| 2008/0276687 A1 | 11/2008 | Myrick et al. | |
| 2008/0309930 A1 | 12/2008 | Rensen | |
| 2009/0002697 A1 | 1/2009 | Freese et al. | |
| 2009/0015819 A1 | 1/2009 | Van Beek et al. | |
| 2009/0033933 A1 | 2/2009 | Myrick | |
| 2009/0073433 A1 | 3/2009 | Myrick et al. | |
| 2009/0097024 A1 | 4/2009 | Blackburn et al. | |
| 2009/0140144 A1 | 6/2009 | Myrick et al. | |
| 2009/0216504 A1 | 8/2009 | Priore et al. | |
| 2009/0219538 A1 | 9/2009 | Myrick et al. | |
| 2009/0219539 A1 | 9/2009 | Myrick et al. | |
| 2009/0250613 A1 | 10/2009 | Myrick et al. | |
| 2009/0299946 A1 | 12/2009 | Myrick et al. | |
| 2010/0042348 A1 | 2/2010 | Bakker | |
| 2010/0073666 A1 | 3/2010 | Perkins et al. | |
| 2010/0141952 A1 | 6/2010 | Myrick et al. | |
| 2010/0149537 A1 | 6/2010 | Myrick et al. | |
| 2010/0153048 A1 | 6/2010 | Myrick et al. | |
| 2010/0182600 A1 | 7/2010 | Freese et al. | |
| 2010/0195105 A1 | 8/2010 | Myrick et al. | |
| 2010/0211329 A1 | 8/2010 | Farquharson et al. | |
| 2010/0245096 A1 | 9/2010 | Jones et al. | |
| 2010/0265509 A1 | 10/2010 | Jones et al. | |
| 2010/0302539 A1 | 12/2010 | Myrick et al. | |
| 2010/0305741 A1 | 12/2010 | Myrick | |
| 2010/0328669 A1 | 12/2010 | Myrick et al. | |

FOREIGN PATENT DOCUMENTS

| | | | |
|---|---|---|---|
| EP | 1974201 A1 | 10/2008 | |
| EP | 2087328 A2 | 8/2009 | |
| EP | 2140238 A1 | 1/2010 | |
| JP | 57142546 A | 9/1982 | |
| WO | 2004/057284 A1 | 7/2004 | |
| WO | 2005/062006 A1 | 7/2005 | |
| WO | 2005/062986 A2 | 7/2005 | |
| WO | 2006/031733 A2 | 3/2006 | |
| WO | 2006/064446 A1 | 6/2006 | |
| WO | 2006/137902 A2 | 12/2006 | |
| WO | 2007/061435 A1 | 5/2007 | |
| WO | 2007/061436 A1 | 5/2007 | |
| WO | 2007/061437 A1 | 5/2007 | |
| WO | 2007/062202 A1 | 5/2007 | |
| WO | 2007/062224 A1 | 5/2007 | |
| WO | 2007/064578 A2 | 6/2007 | |
| WO | WO 2007/064575 A1 | 6/2007 | |
| WO | 2008/002903 A2 | 1/2008 | |
| WO | 2008/057912 A2 | 5/2008 | |
| WO | 2008/057913 A2 | 5/2008 | |
| WO | 2008/121684 A1 | 10/2008 | |

OTHER PUBLICATIONS

E.B. Martin et al., "Process Performance Monitoring Using Multivariate Statistical Process Control", IEE Proc.—Control Theory Appl., vol. 143, No. 2, pp. 132-144, Mar. 1996.
Mandelis et al., "Theory of Photopyroelectric Spectroscopy of Solids", Journal of Applied Physics, vol. 57, No. 9, pp. 4421-4430, 1985.
Zagonel et al., "Multivariate Monitoring of Soybean Oil Ethanolysis by FTIR", Talanta, vol. 63, No. 4, pp. 1021-1025, 2004.
Inon et al., "Combination of Mid- and Near-Infrared Spectroscopy for the Determination of the Quality Properties of Beers", Analytica Chimica Acta, vol. 571, No. 2, pp. 167-174, 2006.
Czarnik-Matusewicz et al., Temperature-Dependent Water Structural Transitions Examined by Near-IR and Mid-IR Spectra Analyzed by Multivariate Curve Resolution and Two-Dimensional Correlation Spectroscopy, Analytica Chimica Acta, vol. 544, No. 1-2, pp. 15-25, 2005.
Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.
Ghesti et al., "Application of Raman Spectroscopy to Monitor and Quantify Ethyl Esters in Soybean Oil Transesterification", Journal of the American Oil Chemists' Society, vol. 83, pp. 597-601, 2006.
Dereniak et al., Infrared Detectors and Systems, John Wiley & Sons: New York, Chapter 9, pp. 395-438, 1996.

Prystay et al., "Thermophysical Measurements and Interfacial Adhesion Studies in Ultrathin Polymer Films Using Homodyne Photothermal Spectrometry", Applied Spectroscopy, vol. 47, No. 4, pp. 501-514, 1993.
Simcock et al, "Tuning D* with Modified Thermal Detectors", Applied Spectroscopy, vol. 60, No. 12, pp. 1469-1476, 2006.
Lang, "Ferroelectric Polymers and Ceramic-Polymer Composites", Key Engineering Materials, vol. 92-93, pp. 83-142, 1994.
Profeta et al., "Spectral Resolution in Multivariate Optical Computing", Spectrochimica Acta Part A: Molecular and Biomolecular Spectroscopy, vol. 67, pp. 483-502, 2007.
Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.
Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.
Knothe, "Analyzing Biodiesel: Standards and Other Methods", Journal of the American Oil Chemists Society, vol. 83, No. 10, pp. 823-833, 2006.
E.D. Palik, Handbook of Optical Constants of Solids I, Academic Press, San Diego, pp. 350-357, 1998.
M.L. Myrick, "Multivariate optical elements simplify spectroscopy", Laser Focus World 38, 91-94, 2002.
O. Soyemi et al., "Design and testing of a multivariate optical element: The first demonstration of multivariate optical computing for predictive spectroscopy", Anal. Chem. 73, No. 6, pp. 1069-1079, (2001).
M.L. Myrick et al., "A single-element all-optical approach to chemometric prediction", Vib. Spectrosc. 28, 73-81, 2002.
A.M.C. Prakash et al., "Optical regression: a method for improving quantitative precision of multivariate prediction with single channel spectrometers", Chemom. Intell. Lab. Syst. 46, 265-274, 1999.
R.A. Deverse et al., "Realization of the Hadamard multiplex advantage using a programmable optical mask in a dispersive flat-field near-infrared spectrometer", Appl. Spectrosc. 54, 1751-1758, 2000.
F.G. Haibach et al., "Precision in multivariate optical computing", Appl. Optics 43, 2130-2140, 2004.
M.L. Myrick et al., "Application of multivariate optical computing to simple near-infrared point measurements", Proceedings of the SPIE, Bellingham, VA, US, vol. 4574, pp. 208-215, 2002.
O.S. Heavens, Optical Properties of Thin Solid Films, Dover Publications, Inc., Mineola, USA, pp. 62-81, 242-249, 1991.
S. Betancourt et al., "Analyzing Hydrocarbons in the Borehole", Oilfield Review, pp. 54-61, Autumn 2003.
D. Eastwood et al., "Field applications of stand-off sensing using visible/NIR multivariate optical computing", Ground and Air Pollution Monitoring and Remediation, SPIE vol. 4199, pp. 105-114, 2001.
Haibach et al., "On-line Reoptimization of Filter Designs for Multivariate Optical Elements", Applied Optics, vol. 42, No. 10, pp. 1833-1838, Apr. 1, 2003.
Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.
M.P. Nelson et al., "Multivariate optical computation for predictive spectroscopy", SPIE Vo. 3261, pp. 232-243, 1998.
O. Soyemi et al., "A Simple Optical Computing Device for Chemical Analysis", Proceedings of SPIE Vo. 4284, pp. 17-28, 2001.
O. Soyemi et al., "Design of angle tolerant multivariate optical elements for chemical imaging", Applied Optics, vol. 41, No. 10, pp. 1936-1941, Apr. 1, 2002.
O. Soyemi et al., "Nonlinear Optimization Algorithm for Multivariate Optical Element Design", Applied Spectroscopy, vol. 56, No. 4, pp. 477-487, 2002.
O. Soyemi et al., "Novel Filter Design Algorithm for Multivariate Optical Computing", Advanced Environmental and Chemical Sensing Technology, Proceedings of SPIE Vo. 4205, pp. 288-299, 2001.
Strausz et al., "About the Colloidal Nature of Asphaltenes and the MW of Covalent Monomeric Units", American Chemical Society, Energy and Fuels 16, No. 4, pp. 809-822, 2002 (abstract).

N. Aske et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 1304-1312, 2001.

N. Aske et al., "Asphaltene Aggregation from Crude Oils and Models Systems Studied by High-Pressure NIR Spectroscopy", Energy and Fuels, American Chemical Society, 16, No. 5, pp. 1287-1295, 2002.

Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.

Y. Yan et al. "Fluorescence Fingerprint of Waters: Excitation-Emission Matrix Spectroscopy as a Tracking Tool", Applied Spectroscopy, vol. 54, No. 10, pp. 1539-1542, 2000.

M.P. Nelson et al., "Multivariate optical computation for predictive spectroscopy", Analytical Chemistry, vol. 70, No. 1, pp. 73-82, Jan. 1, 1998.

M.P. Nelson et al., "Fabrication and evaluation of a dimension-reduction fiberoptic system for chemical imaging applications", Review of Scientific Instruments, vol. 70, No. 6, pp. 2836-2843, Jun. 1999.

M.L. Myrick, "New approaches to implementing predictive spectroscopy", Proceedings of the SPIE Conference on Pattern Recognition, Chemometrics, and Imaging for Optical Environmental Monitoring, SPIE vol. 3854, pp. 98-102, Sep. 1999.

M. Groner et al., "Identification of Major Water-Soluble Fluorescent Components of Some Petrochemicals", Marine Pollution Bulletin, vol. 42, No. 10, pp. 935-941, 2001.

M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.

M.L. Myrick et al., "Spectral tolerance determination for multivariate optical element design", Fresenius J Anal Chem, 369:351-355, 2001.

R.J. Priore et al., "Miniature Stereo Spectral Imaging System for Multivariate Optical Computing", Applied Spectroscopy, vol. 58, No. 7, pp. 870-873, 2004.

M.L. Myrick et al., "Use of Molecular Symmetry to Describe Pauli Principle Effects on the Vibration-Rotation Spectroscopy of $CO_2(g)$", Journal of Chemical Education, vol. 81, No. 3, pp. 379-382, Mar. 2004.

M.N. Simcock et al., "Precision in imaging multivariate optical computing", Applied Optics, vol. 46., No. 7, pp. 1066-1080, Mar. 1, 2007.

Ozturk et al., "Filtering Characteristics of Hybrid Integrated Polymer and Compound Semiconductor Waveguides", In: Journal of Lightwave Technology, vol. 20, No. 8, pp. 1530-1536, Aug. 2002.

P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.

Mullins et al., "Gas-Oil Ratio of Live Crude Oils Determined by Near-Infrared Spectroscopy", Applied Spectroscopy, vol. 55, No. 2, pp. 197-201, 2001.

PCT International Search Report/Written Opinion mailed Apr. 16, 2008, in related Application No. PCT/US2007/083291.

* cited by examiner

SELF CALIBRATION METHODS FOR OPTICAL ANALYSIS SYSTEM

CROSS-REFERENCE TO RELATED APPLICATIONS

This application claims benefit of U.S. Provisional Patent Application Ser. No. 60/740,045, filed Nov. 28, 2005.

FIELD OF THE INVENTION

The present invention relates to spectroscopy analysis systems. More particularly, the invention relates to self-calibration apparatus and methodologies for use with multivariate optical computing systems.

BACKGROUND OF THE INVENTION

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of information for each sample. For example, a polymer sample may be Illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{(Equation 1)}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n_{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \qquad \text{(Equation 2)}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \qquad \text{(Equation 3)}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or coadds measurements at these important wavelengths, the signal increases linearly while the noise increases as a square root of the signal. Another contribution to this measurement precision enhancement is a combination of the Felgott's and Jacquinot's advantage which is possessed by MOE optical computing.

While various methodologies have been developed to enhance measurement accuracy in Optical Analysis Systems, no design has emerged that generally encompasses all of the desired characteristics as hereafter presented in accordance with the subject technology.

SUMMARY OF THE INVENTION

In view of the recognized features encountered in the prior art and addressed by the present subject matter, an improved methodology for calibrating an Optical Analysis System (OAS) has been developed.

In an exemplary configuration, calibration of the OAS may be provided by selective modification of a portion of a light beam.

In one of their simpler forms, modification of the light beam may correspond to selective filtration through known characteristic elements. In another form, modification of the light beam may correspond to selective deflection of the light beam.

Another positive aspect of this type of device is that continuous calibration may be provided by selective, intermittent deflection of portions of a light beam.

In accordance with aspects of certain embodiments of the present subject matter, methodologies are provided to deflect an analyzing light beam through a sample or alternately to a reference determining element.

In accordance with certain aspects of other embodiments of the present subject matter, methodologies have been developed to selectively redirect a light beam for analysis purposes or calibration purposes.

According to one aspect of the invention, a method for calibrating an optical analysis system includes providing an illumination source; providing a sample detector; providing a mirror between the illumination source and the sample detector; modulating a light from the illumination source; providing a reference detector; and modifying at least one characteristic of the light arriving at the sample detector and reference detector from the illumination source, whereby a baseline may be established for measurements taken by the optical analysis system.

According to this aspect, the light may be modulated by a photoelastic modulator. Alternatively, the light may be modulated by a chopper wheel.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Repeat use of reference characters throughout the present specification and appended drawings is intended to represent same or analogous features or elements of the invention.

DETAILED DESCRIPTION OF THE PREFERRED EMBODIMENTS

As discussed in the Summary of the Invention section, the present subject matter is particularly concerned with self calibration of optical analysis systems.

Selected combinations of aspects of the disclosed technology correspond to a plurality of different embodiments of the present invention. It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function.

Figure 1:
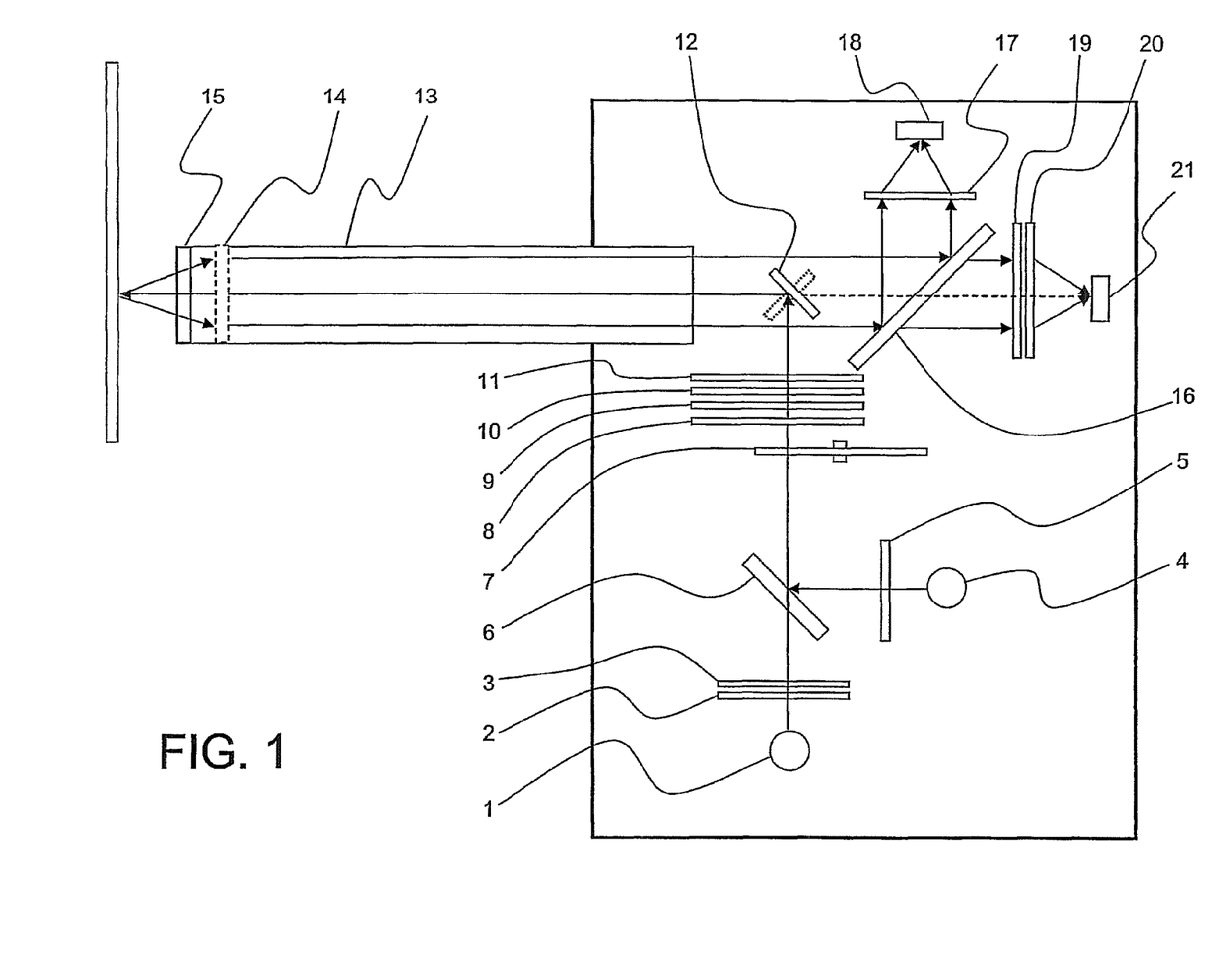
FIG. 1 illustrates a first exemplary embodiment of an optical analysis system constructed in accordance with the present technology.

Reference will now be made in detail to the presently preferred embodiments of the subject self calibrating optical analysis system. Referring now to the drawings, FIG. 1 illustrates an optical analysis system in which an illumination source 1, 4 shines light through a set of lenses 2, 3, 5 and then through a chopper wheel 7 by way of beam splitter 6. Chopper wheel 7 corresponds to a rotating wheel that, in an exemplary configuration, may include ten (10) segments or windows. Chopper wheel 7 may be rotated at about 40 Hz which produces a light beam modulated at about 400 Hz. The chopper wheel 7 could have 2, 3, 5, 20 or other numbers of windows and be rotated at different frequencies to produce required modulations.

As shown in FIG. 1, the light beam passes through one or more spectral elements 8, 9, 10, and lens 11 which control the spectral region of the light passing through them and onto a sample of material being analyzed. The light is reflected by mirror 12 along the center of a sampling tube 13 and focused by lens 14 on a sample being tested. Light is reflected back by the sample through lens 14 and back down the sampling tube 13 past mirror 12. The light passes through beam splitter 16 which reflects a portion of the light through lens 17 onto photodetector 18 and another portion of the light through multivariate optical element (MOE) 19 and lens 20 and onto photodetector 21.

An example of the foregoing spectral elements is a SCHOTT brand filter, which can be a long pass, short pass, or band pass filter. Table 1 provides further examples of the types of detectors that can be used in the optical analysis system.

TABLE 1

| Detector | Types[1] | Wave Range ($\lambda\mu$) | Detectivity $D^2$ | Cut Off Frequency ($H_z$) | Operating Temperature (K) |
|---|---|---|---|---|---|
| Pt—S | PV | 0.35-0.6 | 30 | $10^8$ | 295.0 |
| Si p-n PD | PV | 0.4-1.0 | 50 | $10^7$ | 295.0 |
| Si p-i-n PD | PV | 0.4-1.1 | 80 | $10^8$ | 295.0 |
| Si APD | PV | 0.4-0.8 | 80 | $10^{10}$ | 295.0 |
| Ge p-n PD | PV | 0.6-1.8 | 50 | $10^7$ | 295.0 |
| InSb p-n PD | PV | 3.0-6.2 | 8 | $5 \times 10^2$ | 77.0 |
| PbSnTe p-n PD | PV | 5.0-11.4 | >15-60 V/W | 10 | 77.0 |
| PbS | PC | 0.5-3.8 | 15.00 | 300 | 196.0 |
| PbSe | PC | 0.8-4.6 | 3.00 | $3 \times 10^3$ | 196.0 |
| PbTe | PC | 0.8-5.5 | 0.16 | $3 \times 10^3$ | 196.0 |
| p-InSb | PC | 2.0-6.7 | 2.00 | $2 \times 10^5$ | 77.0 |
| n-InSb | PC | 1.0-3.6 | 30.00 | $2 \times 10^8$ | 195.0 |
| PbSnTe | PC | 5.0-11.0 | 1.7 | $8 \times 10^5$ | 4.2 |
| CdHgTe | PC | 5.0-16.0 | 3.00 | $10^4$ | 4.2 |
| Ge:Au | PC | 2.0-9.5 | 0.02 | $10^4$ | 77.0 |
| Ge:Zn, Au | PC | 5.0-40.0 | 1.00 | $10^3$ | 4.2 |
| Ge:Cu | PC | 5.0-30.0 | 3.00 | $10^3$ | 4.2 |
| Si:Al | PC | 2.0-16.0 | 1.00 | $10^4$ | 27.0 |
| Si:Sb | PC | 2.0-31.5 | 1.80 | $10^4$ | 4.0 |
| ATGS | TC | 1-1000 | 0.030 | 10 | 295.0 |
| (Ba,Sr)TiO$_3$ | TC | 1-1000 | 0.011 | 400 | 295.0 |
| Si | — | 0.2-1.1 | — | — | — |
| Ge | — | 0.4-1.8 | — | — | — |
| InAs | — | 1.0-3.8 | — | — | — |
| InGaAs | — | 0.8-3.0 | — | — | — |
| InSb | — | 1.0-7.0 | — | — | — |
| InSb (77K) | — | 1.0-5.6 | — | — | — |
| HgCdTe (77K) | — | 1.0-25.0 | — | — | — |

Note 1:
PV - photo transistor type; PC: photo conductive detector type; TC: pyroelectric detector type Note 2:
($10^{10}$ cmHz$^{1/2}$ W$^1$)

The illumination sources 1, 4 used in this embodiment of an optical analysis system in accordance with the present technology are chosen to provide a spectral range as determined by the spectral range of interest for the measurement. The sources are also chosen based on criteria including, but not limited to, reliability, intensity, and temperature generation. Redundant sources may be used to provide enhanced reliability. In some instances, when more sources are used, they may be oriented at 90 degrees from each other with a beam splitter located at a center point to provide a constant source of illumination.

One aspect to constructing a system in accordance with the present technology is to maximize the light levels through the system. Correspondingly, there are many points in the design which are configured to enhance the transmission, i.e. reduce loss, of the light signal.

Lenses 2, 5 are used to collect the light from the illumination sources 1, 4, respectively and then to focus the light on chopper wheel 7. Lenses 2 and 5 are designed and positioned to capture as much light as possible from the illumination sources. Lens 3 is used to focus as much light as possible through the chopper wheel 7. The focal length, position and material of construction of the lenses are chosen to reduce as much as possible the loss of the light signal.

Chopper wheel 7 is configured to modulate the light signal to enable the photodetectors to perform properly. In an exemplary configuration, rotation speed and segmentation of the chopper wheel 7 are selected to produce a modulation frequency in the range of 50-5000 Hz. In an exemplary embodiment of the system, a 10-window chopper wheel may be rotating at 40 Hz, providing a chopped signal of 400 Hz. The chopper frequency is chosen past the sampling window, the performance characteristic of the photodetector and amplification system, the sampling rate of the data collection and analysis system and the physical properties of the chopper motor, control system, and wheel (including window materials)

Figure 2A:
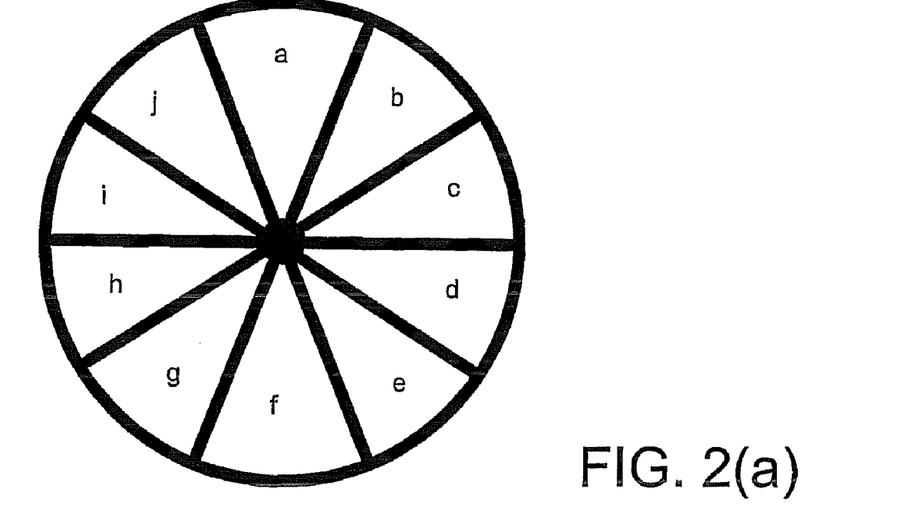
FIGS. 2a and 2b illustrate exemplary chopper wheel configurations as may be employed with an optical analysis system in accordance with the present technology.
Figure 2B:
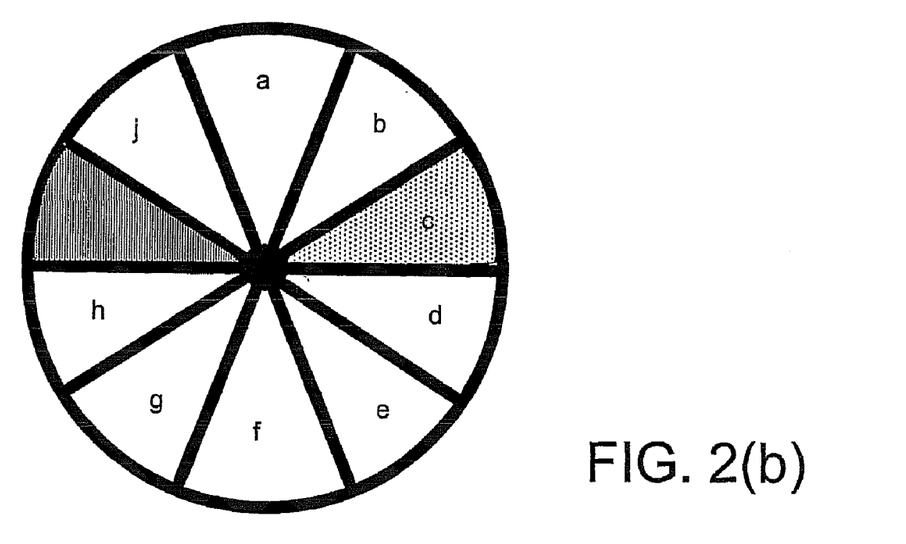

The number of windows in the chopper wheel can be adjusted to provide a suitable degree of signal modulation. In the most basic design, the chopper consists of open windows and black spokes which block the light as shown in FIGS. 2(*a*) and 2(*b*). In a further embodiment, different materials can be placed in the windows to provide different spectral characteristics for the various windows. These window materials are at least somewhat transmissive to the light signal and the transmission characteristic of these windows can be used as further spectral elements. These windows can also contain multivariate optical elements (MOEs). This concept is illustrated in FIG. 2(*b*), where windows labeled "c" and "i" are shown as shaded to indicate that they contain a different material than the other windows. In general, these windows can each be open or transmissive, reflective, refractive, holographic or have other suitable materials.

After the light passes through chopper 7, it passes through another lens 11 and then through the spectral elements 8, 9, 10 chosen based on the application. Individual spectral elements may be chosen based on the chemical materials of interest being analyzed. The spectral elements are chosen so that the spectral region of the illumination covers the desired range.

The light exits the spectral elements and reflects off of mirror 12 and down the sampling tube 13. Lens 14 near the end of the tube 13 focuses the light onto the sample, with a focal point about 0-5 mm into the sample material. The end of the sampling tube may be sealed using a transmissive window. Lens 14 focuses the light past the window into the sample. Using such a window 15 enables a vessel which is being tested/sampled into to remain intact. If the window is not uniformly transmissive across wavelengths, the transmission characteristics of the window should be taken into account for the design of the system and in particular the MOE. further defined (separated) by physically separating the inner and outer regions with another tube. While a small reduction in total light return can be expected if such a tube is used, this loss may be more than offset by improvement in the amount of backscattered radiation returned to the detectors without ever encountering the sample.

The reflected light travels back down the outer annular region of the sampling tube 13 and past the turning mirror 12. The light reaches the beam splitter 16 which divides the beam with a neutral or gray spectrum, sending some of the light through lens 17 onto a first detector 18 and some of the light through a Multivariate Optical Element (MOE) 19, lens 20 and on to a second detector 21.

Because the system as described herein is completely enclosed, it can be used in a dangerous, explosive environment. In general, the system is contained in a box or housing of stainless steel, plastic or other material. The level of hazard of the environment determines the level of containment needed. Sampling is accomplished through a window that is transmissive in the spectral region of interest.

In accordance with the present technology an auto-calibration feature is provided for the Optical Analysis System that may be implemented by various methods. The system as currently configured measures a first signal "A" corresponding to the signal from detector 21 through the multivariate optical element (MOE) and a second signal "B" corresponding to a reference signal from detector 18. The ratio of these two signals may be used to measure the concentration of a chemical of interest. In order to maintain stability and/or reliability in the measurement, an auto-calibration process in accordance with the present subject matter may be implemented to confirm the signals A and B independently or the ratio of A and B.

The auto-calibration process according to the present technology may be performed according to several different methodologies. The following methods are exemplary of the possible methodologies and are not intended as limitations on the full range of methods that may be employed. wheel 7 illustrated in FIG. 1 with more detailed views illustrated in FIGS. 2(*a*) and 2(*b*). Rotation of chopper wheel 7 modulates the light impinging on the sample and hence the photodetector. A first method of the auto-calibration process involves placing a single known material in one or more of the chopper windows. A second method of the auto-calibration process involves providing different known materials in several of the chopper windows. In accordance with the first and second methods, by having knowledge of the composition of the material(s) in the chopper windows, the signal coming from the detector can be determined. The variation in the material(s) in chopper wheel 7 is illustrated by shading of windows "c" and "i" in FIG. 2(*b*). It should be appreciated that, in general, it is not a requirement of the present technology to provide a specific number of windows in the chopper wheel. By using multiple calibration materials in chopper wheel 7, several calibration parameters in the control software can be set, confirmed, or verified, essentially one per calibration material. Table 3 provides sample spectral elements that may be used in the present invention.

Figure 3A:
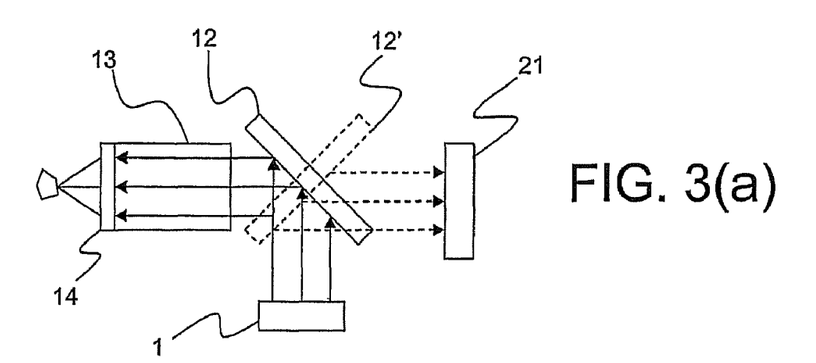
FIGS. 3a, 3b, 3c, and 3d illustrate alternative exemplary embodiments of mirror assemblies usable with an optical analysis system constructed in accordance with the present technology.

A third calibration method of the auto-calibration process involves a movable mirror 12 (FIG. I), positioned so that, either by turning or horizontal displacement, the light that is normally directed down the sampling tube 13 would be directed toward the beam splitter 16 and hence the detectors without encountering the sample. A first configuration of this third calibration methodology is illustrated in FIG. 3(*a*) In this configuration, viewed from above, mirror 12 can be positioned so that the illumination light beam is directed down the sampling tube 13 toward the sample focusing lens 14. During calibration, mirror 12 is turned toward position 12' shown in a phantom view in FIG. 3(*a*) In this position, the light is directed from the illumination source and chopper wheel 7 to the beamsplitter 16 (FIG. 1) and then the detectors 18,21 by way of beam splitter 16. Beam splitter 16 and detector 18 seen in FIG. 1 have been omitted for clarity in FIG. 3(*a*).

TABLE 2

| Material | Comments | SWL cm−1 | LWL cm−1 | RI | Solubility g/100 g | Hardness Kg/mm 2 | MP °C. | pH Range |
|---|---|---|---|---|---|---|---|---|
| AMTIR | SeAsGe glass | 11000 | 593 | 2.5 | 0 | 170 | 370 | 1-9 |
| BaF2 | Barium Fluoride | 66600 | 691 | 1.45 | 0.17 | 82 | 1280 | 5-8 |
| CaF2 | Calcium Fluoride | 79500 | 896 | 1.4 | 0.0017 | 158 | 1360 | 5-8 |
| CsI | Cesium Iodide | 42000 | 172 | 1.73 | 44 | 20 | 621 | NA |
| Diamond | Type IIa, strong IR absorbance between 2700-1800 cm−1 | 30000 | <2 | 2.4 | 0 | 5700 | 550 fp | 1-14 |
| Ge | Germanium, becomes opaque at elevated temperatures | 5500 | 432 | 4 | 0 | 780 | 936 | 1-14 |
| KBr | Potassium Bromide | 48800 | 345 | 1.52 | 53 | 6 | 730 | NA |
| KCl | Potassium Chloride | 55600 | 385 | 1.45 | 35 | 7 | 776 | NA |
| KRS-5 | Thallium Bromide/ Thallium Iodide | 17900 | 204 | 2.37 | 0.05 | 40 | 414 | 5-8 |
| NaCl | Sodium Chloride | 52600 | 457 | 1.49 | 36 | 18 | 801 | NA |
| Polyethylene | For Far-IR, swells with some organic solvents | 625 | <4 | 1.52 | 0 | | 110 | 1.5-14 |
| SiO2 | Silicon Dioxide | 50000 | 2315 | 1.53 | 0 | 460 | 1713 | 1-14 |
| Si | Silicon, strong IR absorbance between 624-590 cm−1 | 8900 | 624.30 | 3.41 | 0 | 1150 | 1420 | 1-12 |
| ZnS | Zinc Sulfide | 17000 | 690 | 2.2 | 0 | 240 | 1830 | 5-9 |
| ZnSe | Zinc Selenide | 15000 | 461 | 2.4 | 0 | 120 | 1526 | 5-9 |

Figure 3B:
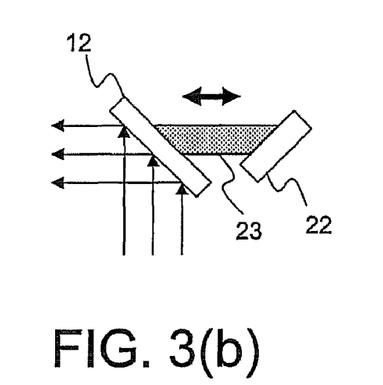
Figure 3C:
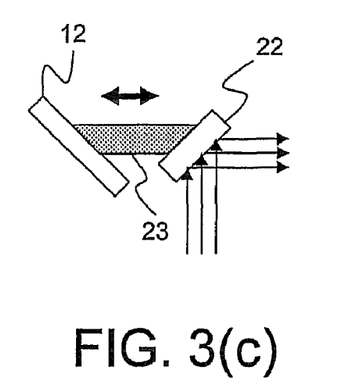

To convert from wavenumber (cm−1) to wavelength (gm), divide 10,000 by the wavenumber such that 5500 cm−1 is equivalent to 1.81 m or 1800 nm.
SWL—Shortest wavelength for transmission, 1 mm, 50% transmission
LWL—Longest wavelength for transmission, 1 mm, 50% transmission
RI—Refractive Index, at relevant wavelength
MP—Melting point
pH - negative log of hydrogen ion concentration An embodiment of a movable mirror methodology is illustrated in FIGS. 3(b) and 3(c) where the mirror assembly 12, 23, 22 is configured to move horizontally in the direction of the double ended arrow with mirror 12 angled to direct light down the sampling tube 13 and mirror 22 angled to direct light toward beamsplitter 16. During normal sampling mirror 12 may be positioned as illustrated in FIG. 3(b). For calibration, the mirror assembly would be moved as in FIG. 3(c).

It should be appreciated that it may be necessary to adjust the gain on this "bypass." Alternatively, calibration materials that transmit a lower amount of light can be chosen so that the detectors can be kept at the same gains used for measuring the sample. Detectors provide an increased output signal dependent upon the amount of light impinging on them. As such, there is a preferred operating region for the detectors and subsequent amplification of the signal such that the final output does vary with the amount of impinging light. For instance, there are levels of light that are too low to produce a reliable output signal. In addition, there are levels of light that are too great and overload the detection system. At these high light levels, changes in the amount of light do not change the output signal. The preferred mode of operation is where the amount of light is in the range where there is a good correlation between the amount of light and the output signal of the detector system.

In accordance with the present auto-calibration technology, light is directed from the illumination sources 1, 4 to the detectors 18, 21 without interacting with the sample. Depending upon the type of sample being analyzed and the transmission characteristic of the light path between the illumination source, the sample, and the detectors, there can be a range of signals returned to the detector. As an example, the light path could include a fiber optic probe or the sample could be a powder being measured in a reflectance mode. In both of these examples, the amount of light returning to the detectors during normal sampling could be significantly less than the amount of light following the by-pass or calibration route to the detectors. In an exemplary configuration, light transmission through a sample may be reduced from 50-99.9%. Thus, in order to enable the detector and amplification system to operate over a useful range, some attenuation of the signal in the calibration elements may be needed.

Figure 3D:
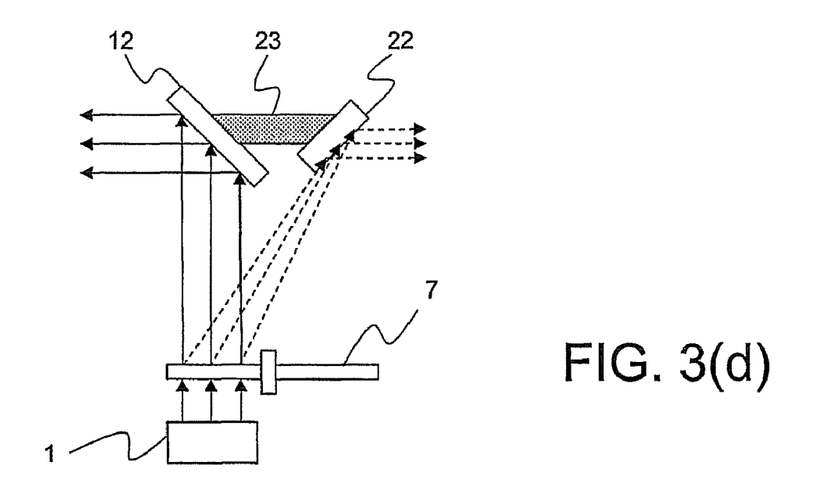

In accordance with the present auto-calibration technology, a fourth calibration methodology involves providing an element in chopper wheel 7 that turns the light path slightly in addition to having a known spectral characteristic. As illustrated in FIG. 3(d), light can be directed to a reflective surface 22 that sends light to the beam splitter 16 and then detectors 18, 21. A particular aspect to this embodiment is that it allows for a continuous or real time check of the instrument calibration with each rotation of chopper wheel 7. In accordance with this method a stationary mirror assembly 12, 22, 23 allows the un-deflected beam to pass to the sample for sample measurements and the deflected beam to be directed toward the detection system without passing through or encountering the sample.

Figure 4:
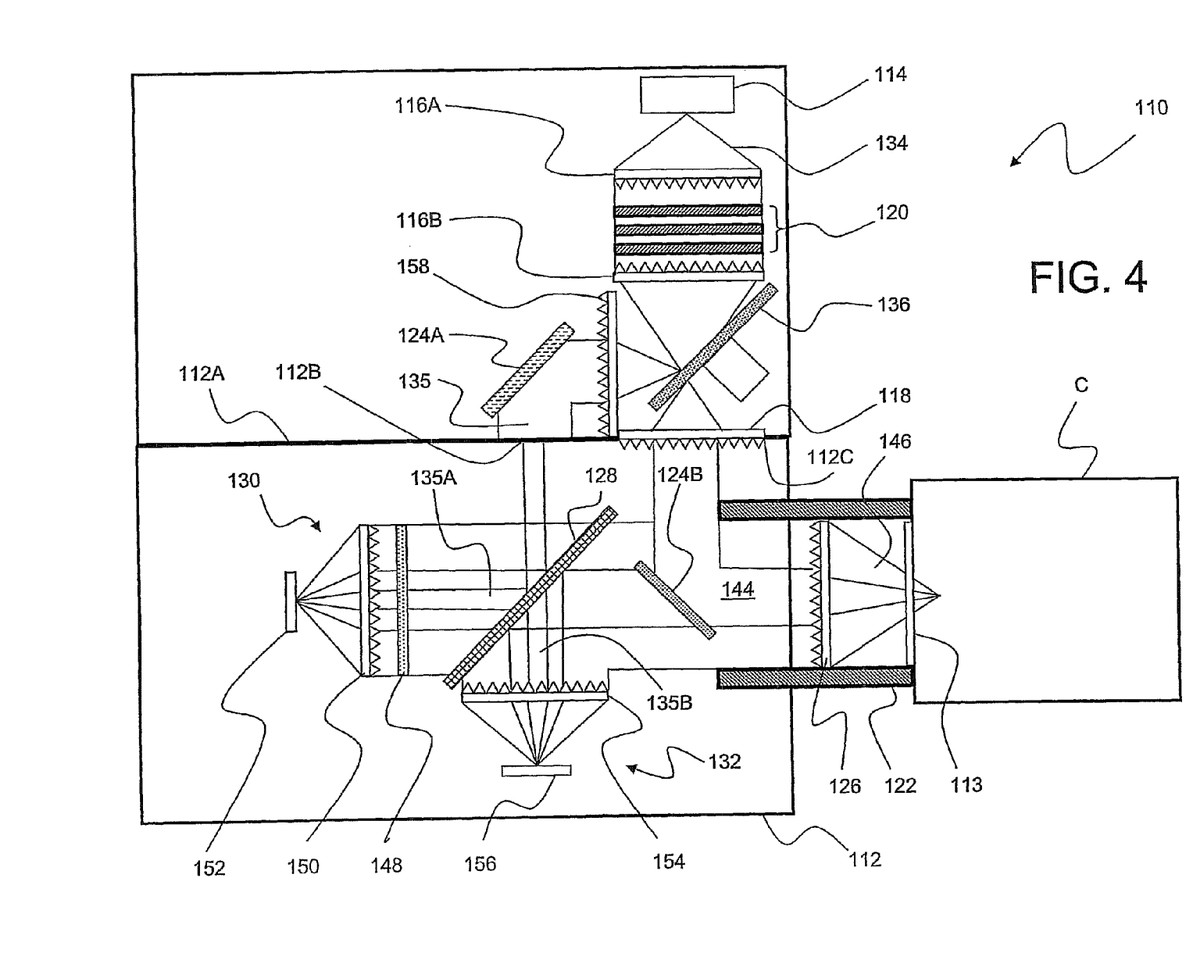
FIG. 4 illustrates a second exemplary embodiment of an optical analysis system constructed in accordance with the present technology.

With reference now to FIG. 4, a second exemplary embodiment of the present subject matter is designated generally by reference number 110. Many aspects of the optical analysis system 110 and related components are similar to the foregoing embodiment; thus, for the sake of brevity only certain differences are described below. However, to provide a full and enabling disclosure of the optical analysis system 110, when like or similar elements and components are not specifically described below; Implicit reference is made to the foregoing descriptions.

As shown in FIG. 4, the optical analysis system 110 broadly includes a housing 112, an illumination or light source 114, a chopper wheel 136, a plurality of spectral elements 120, a focusing lens 126, a beam splitter 128, a first detector 130 including a multivariate optical element 148 and a second detector 132. As shown, the illumination source 114 provides a light 134, which passes through a collecting Fresnel lens 116A and into and through the spectral element(s) 120. In this example, the illumination source 114 is rated for at least about 10,000 hours of operation, which alleviates a need for redundant illumination sources though they may be provided if desired. Also in this example, the collecting Fresnel lens 116A is sized to be about 1.5 square inches and is spaced about 0.6 inches from the illumination source 114. The skilled artisan will instantly recognize that these dimensions can be adjusted according to particular system requirements and are not meant as limitations of the invention.

Light 134 passes through the spectral elements 120, which filter out undesired wavelengths in order to bound a desired spectral region, e.g., 1500-2000 nm, in order to target a particular chemical material of interest. Light 134 is focused by focusing Fresnel lens 116B, which is also sized to be about 1.5 square inches and spaced about 1 inch to about 3 inches from the chopper wheel 136. As shown, the chopper wheel 136 reflects a portion of light 134 as a calibration or reference light 135 and a transmitted light 144. Calibration light 135 is collimated by lens 158 before reflecting from a first mirror 124A through an adjustable aperture 112B in a bulkhead 112A of the housing 112. The aperture 112B is adjustable to dictate a desired amount of the calibration light 135. Finally, calibration light 135 impinges on beam splitter 128 thereby sending a portion 135A of calibration light 135 to the first MOE detector 152 and a portion 135B of calibration light 135 to the second or baseline detector 156.

FIG. 4 further illustrates that transmitted light 144 passes from the chopper wheel 136 into a collimating Fresnel lens 118, which in this example is sized to be about 1.5 square inches and is spaced from about 0.5 to about 1.5 inches from the chopper wheel 136. The transmitted light 144 passes through another adjustable aperture 112C in the bulkhead 12A and impinges upon a second mirror 124B, which directs the transmitted light 144 toward a sample in a container C, such as mixing vat or blender. The skilled artisan will recognize that the container could be a conveyor belt or other device for holding or transporting the sample and is not limited to an enclosed container.

As shown in FIG. 4, the transmitted light 144 is focused by the focusing Fresnel lens 126, which in this example may be round and about 1 inch in diameter and is adjustable with an inner tube 122. Also in this example, lens 126 may be positioned about 0.6 inches from an outer surface of the container C. As shown, the transmitted light 144, now focused, passes through a transmissive window 113, which in this example is approximately 1 inch in diameter and includes an anti-reflective (AR) coating on either or both sides. The window 113 provides a physical separation between the system 110 and a chemical process in the container C to ensure that the chemical process does not interfere with the measuring process of the optical analysis system 110, and likewise that the electrical functions of the system 110 do not interfere with the chemical process. The AR coating improves the signal by reducing interfering reflectances.

As further shown in FIG. 4, the transmitted light 144 enters the container C and reflects from the sample as a carrier light 146. Those skilled in the art will appreciate that the sample can be a moving mixture such as a chemical mixture, a pharmaceutical blend, a food process, a chemical process; more specifically, such as an aspirin and an excipient being blended in real time, or a plurality of tablets passing by on a conveyor belt at high speed, or milk mixed with vitamins.

FIG. 4 further illustrates that the carrier light 146 is directed by the tube 122 in a direction of the first detector 130. Eventually, the carrier light 146 impinges on the beam splitter 128 and a portion passes in a direction of the detector 132 for baselining with the portion 135B of the calibration light 135. Another portion of the carrier light 146 passes through MOE 148, which as noted above, has been designed based on the chemical(s) of interest and the various components of the system 110. Finally, that portion of the carrier light 146, having passed through the MOE 148, is focused by lens 150 and received by the detector 152. As described above, the two signals collected by the detectors 132 and 152 can be manipulated, e.g., mathematically, to extract and ascertain information about the sample carried by the carrier light 146.

Due to variations in system optical and electronic performance combined with changes in sample reflectance, the Optical Analysis System 110 may use a reference signal (and detector) to account for those variations. For a system with small such variation, it would be possible to use a single detector (with the MOE). In this case, the response from the reference detector would be considered a constant.

Specifically, for improved detector performance, the light signal can be modulated by continuously monitoring the intensity of a beam of light. The easiest way to achieve this is to allow the beam to impinge upon some kind of photoelectric detector (such as a photo-diode or photo-multiplier tube) and monitor the resultant electrical output. If the light beam is very weak then the electrical output from the photodetector will be very small and therefore some sort of amplification of this signal will be required.

A continuous optical beam will create a DC signal at the output of the photo-detector so any subsequent amplifier used to increase this signal level will need to be capable of amplifying DC. Although this is perfectly feasible, DC amplifiers do suffer from drift due to temperature fluctuations. This is particularly evident in high gain amplifiers. Also any other perturbation of the signal due to other stimuli (stray light for example) will also be amplified and appear as genuine output.

If the signal of interest (that is the original light beam) could be made to act as an AC signal then the detector output would be AC and any further amplification could be carried out with an AC (only) amplifier. AC amplifiers do not suffer from temperature drift and will not respond to DC signals. So the only signal that would be amplified is that due to the (AC) light beam. To make a light beam act in an AC manner it needs to be turned on and off regularly and accurately. This can be achieved by chopping.

The most common technique is to pass the beam through a rotating disk that has holes or slots cut into it at regular intervals. As the disk rotates it "chops" the beam producing an on/off signal which when detected by a photo-detector will appear as an AC signal.

The mechanical chopping of the light beam is very precisely controlled by the chopper and therefore the resultant AC signal due to the chopped light is at a known and stable frequency which can be monitored and amplified easily.

The operating principle of a photoelastic modulator (PEM) modulates light polarization which manifests the photoelastic effect in which a mechanically stressed sample exhibits optical birefringence.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

That which is claimed is:

1. A method for calibrating an optical analysis system, comprising:
   providing an illumination light from a source;
   providing a sample detector and a reference detector;
   providing a mirror between a sample and the combination of the sample detector and the reference detector;
   directing the illumination light to the sample in a first measurement, and alternately to the sample detector and the reference detector in a second measurement using the mirror; and
   modifying at least one characteristic of the illumination light arriving at the sample detector and reference detector,
   establishing a baseline by measuring the illumination light directed by the mirror to the sample detector and the reference detector in the second measurement, for measurements taken by the optical analysis system.

2. The method of claim 1 wherein modifying at least one characteristic of the illumination light comprises modulating the illumination light.

3. The method of claim 2, wherein modulating the illumination light is performed by a photoelastic modulator.

4. The method of claim 2, wherein modulating the illumination light is performed by a chopper wheel.

5. The method of claim 1 wherein modifying at least one characteristic of the illumination light comprises placing a plurality of spectral elements between the source and the sample detector and the reference detector.

6. The method of claim 5 wherein the plurality of spectral elements comprises at least one multivariate optical element (MOE).

7. The method of claim 6 wherein at least one MOE is placed between the source and the sample detector.

8. The method of claim 1 wherein the sample detector and the reference detector are the same and a multivariate optical element (MOE) is placed in front of the detector.

9. A method for calibrating an optical analysis system, comprising the steps of:
   providing an illumination light from a source;
   providing a sample detector and a reference detector;
   providing a mirror between a sample and the combination of the sample detector and the reference detector;
   directing the illumination light to the sample in a first measurement, and alternately to the sample detector and the reference detector in a second measurement using the mirror;
   providing a chopper wheel having a predetermined number of windows between the illumination source and the mirror to produce a modulation of the light provided by the illumination source; and
   establishing a baseline by measuring the illumination light directed by the mirror to the sample detector and reference detector in the second measurement for measurements taken by the optical analysis system.

10. The method of claim 9, where the step of directing the illumination light comprises periodically turning the mirror so that the illumination light is alternately directed to the sample and to the sample detector and the reference detector.

11. The method of claim 9, further comprising the step of placing at least one material having a known spectral characteristic in at least one of the predetermined windows of the chopper wheel.

12. The method of claim 9, further comprising the step of placing at least two materials having known spectral characteristics in at least two separate predetermined windows of the chopper wheel.

13. The method of claim 9 further comprising the step of modifying at least one characteristic of the illumination light arriving at the sample detector and reference detector.

14. The method of claim 13, wherein the step of modifying at least one characteristic of the illumination light comprises placing a light turning element in the chopper wheel.

15. The method of claim 14, wherein the light turning element has a known spectral characteristic.

16. The method of claim 14, further comprising the step of placing at least one known material having a known spectral characteristic in at least one of the predetermined windows of the chopper wheel.

17. The method of claim 14, further comprising the step of placing at least two materials having known spectral characteristics in at least two separate predetermined windows of the chopper wheel.

18. The method of claim 9 wherein the sample detector and the reference detector are the same and a MOE is placed in front of the detector.

19. A self-calibrating optical analysis system, comprising:
   an illumination source;
   a sample detector and a reference detector;
   a mirror between the illumination source and a combination of the sample detector and the reference detector to direct a light provided by the illumination source through a sample in a first measurement and alternately to the sample detector and the reference detector in a second measurement;
   a chopper wheel having a predetermined number of windows positioned between the illumination source and the mirror to produce a modulation of the light provided by the illumination source; and,
   whereby a baseline is established by measuring the light from the illumination source directed by the mirror to the sample detector and reference detector in the second measurement for measurements taken by the optical analysis system.

20. The system of claim 19, further comprising a means for turning the mirror so that light from the illumination source is alternately directed to the sample detector and the reference detector.

21. The system of claim 19, further comprising at least one material having a known spectral characteristic placed in at least one of the predetermined windows of the chopper wheel.

22. The system of claim 19, further comprising at least two materials having known spectral characteristics placed in at least two separate predetermined windows of the chopper wheel.

23. The system of claim 19 further comprising a means for modifying at least one characteristic of light arriving at the sample detector and reference detector from the illumination source.

24. The system of claim 23, wherein the means for modifying at least one characteristic of light comprises at least one light turning element positioned in at least one window of the chopper wheel.

25. The system of claim 24, wherein the light turning element has a known spectral characteristic.

26. The system of claim 24, further comprising at least one material having a known spectral characteristic material placed in at least one of the predetermined windows of the chopper wheel.

27. The system of claim 24, further comprising at least two materials having known spectral characteristics placed in at least two separate predetermined windows of the chopper wheel.

28. The system of claim 19 wherein the sample detector and the reference detector are the same and a MOE is placed in front of the detector.

29. A self-calibrating optical analysis system, comprising:
an illumination source;
a sample detector and a reference detector;
a first mirror, and a second mirror placed at a distance from the first mirror, the first mirror and the second mirror placed between a sample and the combination of the sample detector and the reference detector to direct a light provided by the illumination source through the sample in a first measurement, and alternately to the sample detector and the reference detector in a second measurement;
a chopper wheel having a predetermined number of windows positioned between the illumination source and the first mirror to produce a modulation of the light provided by the illumination source; wherein
a baseline is established by measuring the light from the illumination source directed to the sample detector and reference detector in the second measurement for measurements taken by the optical analysis system; and further wherein
at least one light turning element is positioned in at least one window of the chopper wheel, wherein light from the illumination source may be directed by the at least one light turning element to said reference detector by way of the second mirror when the at least one window of the chopper wheel is placed between the illumination source and the first mirror.

30. The system of claim 29, further comprising a housing wherein the illumination source, the chopper wheel and the second mirror are separated from the first mirror, the sample detector and the reference detector.

31. A method for calibrating an optical analysis system, comprising:
placing an optical element between a sample and a combination of a sample detector and a reference detector;
directing, with the optical element, a light provided by an illumination source through the sample in a first measurement and alternately to the sample detector and the reference detector in a second measurement;
modifying at least one characteristic of the light arriving at the sample detector and reference detector from the illumination source; and
establishing a baseline by measuring the light from the illumination source to the sample detector and the reference detector in the second measurement, for measurements taken by the optical analysis system.

32. A method for calibrating an optical analysis system, comprising the steps of:
placing an optical element between a sample and a combination of a sample detector and a reference detector;
directing, with the optical element an illumination, light to the sample in a first measurement and alternately to the sample detector and the reference detector in a second measurement;
modulating the illumination light using a chopper wheel having a predetermined number of windows,
establishing a baseline by measuring the illumination light directed to the sample detector and reference detector in the second measurement for measurements taken by the optical analysis system.

33. The method of claim 32 wherein directing the illumination light comprises:
coupling a first mirror to a second mirror;
directing the illumination light via the first mirror through the sample in the first measurement;
displacing the coupled first mirror and second mirror so that the illumination light is directed via the second mirror to the sample detector and the reference detector in the second measurement.

34. The method of claim 33 wherein the sample detector and the reference detector are the same and a MOE is placed in front of the detector.

35. A self-calibrating optical analysis system, comprising:
a sample detector and a reference detector;
an optical element placed between a sample and a combination of the sample detector and the reference detector;
a source providing an illumination light to the sample in a first measurement and alternately providing the illumination light to the sample detector and the reference detector in a second measurement with the optical element; and
a chopper wheel having a predetermined number of windows positioned between the source and the sample detector and the reference detector to produce a modulation of the illumination light,
wherein a baseline is established by measuring the light from the source provided to the sample detector and reference detector in the second measurement for measurements taken by the optical analysis system.

36. The system of claim 35, wherein the optical element comprises:
a first mirror disposed between the source and the combination of the sample detector and the reference detector; and
a second mirror coupled to the first mirror, and wherein displacement of the coupled first mirror and the second mirror alternately directs the illumination light from the first mirror to the sample in the first measurement and from the second mirror to the sample detector and the reference detector in the second measurement.

37. The system of claim 36 wherein the sample detector and the reference detector are the same and a MOE is placed in front of the detector.

* * * * *